(12) United States Patent
Do Quang et al.

(10) Patent No.: US 11,680,937 B2
(45) Date of Patent: Jun. 20, 2023

(54) DETECTION AND CHARACTERIZATION OF ANOMALIES IN A CONTINUUM OF WATER

(71) Applicant: SUEZ INTERNATIONAL, Paris la Defense (FR)

(72) Inventors: Zdravka Do Quang, Bailly (FR); Guillaume Cussonneau, Paris (FR); Gilles Fay, Paris (FR)

(73) Assignee: SUEZ INTERNATIONAL, Paris (FR)

( * ) Notice: Subject to any disclaimer, the term of this patent is extended or adjusted under 35 U.S.C. 154(b) by 264 days.

(21) Appl. No.: 16/651,685

(22) PCT Filed: Sep. 26, 2018

(86) PCT No.: PCT/EP2018/076187
§ 371 (c)(1),
(2) Date: Mar. 27, 2020

(87) PCT Pub. No.: WO2019/063648
PCT Pub. Date: Apr. 4, 2019

(65) Prior Publication Data
US 2020/0264151 A1 Aug. 20, 2020

Related U.S. Application Data

(60) Provisional application No. 62/565,722, filed on Sep. 29, 2017.

(30) Foreign Application Priority Data
Dec. 27, 2017 (FR) ....................... 1763286

(51) Int. Cl.
*G01N 33/18* (2006.01)
*G06N 20/10* (2019.01)
(Continued)

(52) U.S. Cl.
CPC ............. *G01N 33/18* (2013.01); *G06N 20/10* (2019.01); *G01N 21/33* (2013.01); *G01N 27/06* (2013.01)

(58) Field of Classification Search
CPC ........ G01N 33/18; G01N 20/10; G01N 21/33; G01N 27/06
See application file for complete search history.

(56) References Cited

U.S. PATENT DOCUMENTS

2008/0178663 A1 * 7/2008 Yang ..................... G01N 1/10
73/61.41

FOREIGN PATENT DOCUMENTS

EP 3 112 960 A1 1/2017
EP 3112960 A1 * 1/2017 ......... G05B 13/0265
(Continued)

*Primary Examiner* — Rebecca C Bryant
(74) *Attorney, Agent, or Firm* — BakerHostetler

(57) ABSTRACT

A device for detecting and characterizing anomalies in a water continuum is provided. The device is configured to receive measurements of physical quantities on the basis of sensors situated in the water continuum. The measurements are thereafter transformed, and a detection of anomalies is performed by a detector of anomalies which is trained with transformed values arising from the same sensors. In parallel with the detection, predefined rules make it possible to characterize a possible anomaly. Thus, an anomaly detection can be optimized for a water continuum in particular, whilst characterization with predefined rules allows the device to be operational without each anomaly having needed to be detected in this water continuum in particular.

18 Claims, 10 Drawing Sheets

(51) Int. Cl.
*G01N 21/33* (2006.01)
*G01N 27/06* (2006.01)

(56) References Cited

FOREIGN PATENT DOCUMENTS

| WO | 2004/063964 A2 | | 7/2004 | |
|---|---|---|---|---|
| WO | WO-2004063964 A2 | * | 7/2004 | ............. G01N 33/18 |
| WO | 2016/012972 A1 | | 1/2016 | |

* cited by examiner

DETECTION AND CHARACTERIZATION OF ANOMALIES IN A CONTINUUM OF WATER

CROSS-REFERENCE TO RELATED APPLICATIONS

This application is a National Stage of International patent application PCT/EP2018/076187, filed on Sep. 26, 2018, which claims priority U.S. Provisional Patent Application No. 62/565,722, filed Sep. 29, 2017, and to foreign French patent application No. FR 1763286, filed on Dec. 27, 2017, the disclosures of which are incorporated by reference in their entireties.

FIELD OF THE INVENTION

The present invention relates to the field of water management, in water distribution networks or natural spaces. More particularly, the present invention relates to the detection of anomalies affecting water quality.

BACKGROUND

Water distribution networks can be affected by numerous anomalies affecting water quality. For example, the water may be contaminated by various pollutants introduced intentionally or unintentionally by water backflow or by connection error, by particles of matter settling regularly in the pipes and suddenly returned to suspension, by reaction with the constituent materials of the networks, or by bacteria during bacterial regrowth phenomena. In order to forestall the deleterious effects that could be caused by contamination, or more generally by a reduction in water quality that could cause discomfort to users (change of color, of taste, of odor . . . ), any event affecting water quality should be detected and characterized as fast and accurately as possible. Problems which alter the quality of the water can also occur in systems, natural water courses or expanses such as lakes, ponds or rivers or set of natural water courses and expanses. These systems may for example be affected by accidental pollution, or the abnormal growth of algae, significantly degrading their state and preventing their use (potabilization, bathing waters . . . ).

The detection of such anomalies may in certain cases turn out to be indispensable, in order to undertake corrective actions to correct the anomaly. The various anomalies occurring in an aquatic system can be detected by monitoring a set of physical parameters in the water. For example, an abnormally low value of the parameters such as the concentration of chlorine or abnormally high value for the turbidity may make it possible to detect an anomaly.

However, this task can sometimes turn out to be difficult, for several reasons. On the one hand, the detection of an anomaly requires the deployment of sensors, to get precise information on the physico-chemical parameters of the water. On the other hand, it can sometimes be difficult, on the basis of sensor measurements, to distinguish normal variations of physical parameters of the water, which are due to the various hydraulic operations required for the proper operation of the network, from abnormal values manifesting an anomaly. In particular, the specific configuration of each system can confer specific values on it. For example, the chlorine concentration can differ significantly within a potable water distribution network, depending on whether one is situated close to a facility or a chlorination point or in remote zones having a long residence time. The quality of the treated water can also vary in a more or less regular way according to the various types of resources available throughout the year. It is then necessary to be able to detect whether an unspecified mixture is encountered.

In order to propose more precise detection of the anomalies affecting a water distribution network, the applicant has filed a patent, published under the number WO 2016/012972. Patent WO 2016/012972 discloses a method for detecting anomalies in a distribution network, which method is particularly suited to a potable water distribution network, consisting in acquiring measurements from one or more sensors on the distribution network, forming time series of sensor measurements, extracting operational characteristics from sensor measurements, forming a vector of operational characteristics, and detecting an anomaly if the vector is significantly dissimilar from previously constructed vectors.

This method allows precise and effective detection of anomalies on a water distribution network, since the detection of anomalies is performed by comparing a vector with transformed vectors arising from the same sensors on one and the same water distribution network. This makes it possible to obtain detection which is completely suited to the characteristics of the water distribution network under study. For example, in an aquatic system consisting of various resources, waters having a different composition (conductivity, temperature, pH . . . ) will usually be seen to alternate at the points of consumption. In such a system, an anomaly might be detected if a combination differing significantly from the usual combinations of these parameters appears, reflecting a new mixture of water. Moreover, the sensitivity of the method can be defined, for the various types of events and measurements.

However, this method may require a lengthy training time before exhibiting fully operational characterization of anomalies. Indeed, detection and identification of a particular type of anomaly on the basis of this method would require that several vectors representative of this anomaly have been constructed and labeled, and therefore that the anomaly has already occurred, in this aquatic system, repeatedly. Such a method would therefore not be fully effective in detecting the anomalies in a given aquatic system until after a sufficiently substantial duration (of possibly as much as several years) such that all the anomalies sought have already occurred repeatedly in the aquatic system under study.

There is therefore a need for detection of anomalies in a water distribution network, making it possible to detect and characterize in a precise manner the events affecting water quality, which is able rapidly to detect and characterize a set of anomalies envisaged in a new aquatic system, for which there is little historical data.

SUMMARY OF THE INVENTION

To this effect, the invention describes a device able to detect and characterize anomalies in a water continuum, comprising: at least one communication link, respectively to at least one sensor of at least one physical quantity in the water continuum; a processor configured to: receive measurements from the at least one sensor through the at least one communication link; generate a plurality of time windows of the measurements; for each time window of said plurality: obtain a set of values transformed by at least one transformation of the measurements over the time window; apply a detector of anomalies to the set of transformed values so as to detect a normal or abnormal state of the time window, said detector of anomalies being parameterized on the basis of sets of transformed values arising from the application of the at least one transformation to time windows of previous measurements of the at least one sensor; detect an anomaly in the water continuum, as a function of a number of time windows exhibiting an abnormal state; execute on the measurements a set of predefined detection rules for detecting a variation of one at least of the physical quantities; if an anomaly in the water continuum is detected, assign to the anomaly an anomaly type associated with a variation of a subset of the physical quantities, if the variation of one at least of the quantities of the subset is detected.

This allows effective detection of the anomalies in the water continuum. Indeed, the detector is parameterized by learning on measurements arising from the same sensors in the same water continuum. Thus, the detector of anomalies is parameterized on the basis of measurements taking into account the particularities of the water continuum, thereby allowing optimized detection of the occurrence of abnormal situations.

An anomaly is typed, once detected, on the basis of predefined rules. This makes it possible to identify, on the basis of general rules, what type the anomaly would be, once the anomaly has been detected. This therefore makes it possible to identify the type of the anomaly, even if this anomaly has not yet been detected in the water continuum with the measurements of the at least one sensor.

The device of the invention therefore makes it possible to obtain at the same time precise detection, based on a parameterization specific to the water continuum, of the occurrence of an abnormal situation, and a general typing of the anomaly based on global knowledge of the effects of the various anomalies, even if the anomaly has not been detected in the water continuum.

Advantageously, one of the transformations of the measurements over a time window is a transformation of the measurements into values representative of the variability of the measurements within the time window.

This makes it possible to detect anomalies that are manifested by a fast variation of a physical quantity in the water continuum. For example, a fast variation of the turbidity can be representative of movements of particles. A transformation of the measurements into values representative of the variability of the measurements of the turbidity within the time window can therefore make it possible to obtain transformed values allowing detection of anomalies of this type.

Advantageously, the transformation of the measurements into values representative of the variability of the measurements within the time window is carried out by subtracting from each measurement over the time window a median of said measurements over a sliding time window comprising at least said time window.

This makes it possible to circumvent the slow variations, for example on the scale of a day, of the measurements over a time window. This transformation exhibits the advantage, in addition to providing in a reliable manner transformed values representative of the variability of the measurements within the time window, of being simple to implement and of requiring restricted calculation power in order to execute.

Advantageously, the transformation preserves only measurements corresponding to a predefined direction of variation.

This allows more effective detection of anomalies manifested by a fast variation of the measurements in a given direction. For example, movements of particles can be manifested by a fast increase in turbidity. Thus, preserving only the measurements corresponding to an increase in turbidity can make it possible to discern this anomaly in a more assured manner.

Advantageously, one of the transformations of the measurements over a time window consists of a slope test over the time window.

This makes it possible to detect anomalies affecting by slow trends of a physical quantity. For example in a potable water network, a slow increase in the number of bacteria, possibly coupled with a slow decline in the chlorine concentration, can signify the risk of appearance of a bacterial growth anomaly. It is advantageous to alert the operational staff regarding this type of ongoing phenomenon so that they are tracked and possibly corrected. In a natural aquatic system, an increase in chlorophyll-a over several days which gives rise firstly to an increase and then a progressive decrease in dissolved oxygen may signify the appearance of algae growth phenomena. They risk being detrimental to aquatic life and to the use of the system, and must therefore be anticipated. A slope test over a time window advantageously makes it possible to detect slow variations such as these, and therefore possible underlying anomalies.

Advantageously, the slope test is a Mann-Kendall trend test.

The Mann-Kendall test allows effective detection of the significant slope.

Advantageously, at least two of the sensors are sensors of one and the same physical quantity at two points of the water continuum, and one of the transformations of the measurements over a time window comprises a time difference between the measurements of the two sensors.

This makes it possible to detect anomalies that are manifested by abnormal evolutions of physical quantities between various points of the continuum.

Advantageously, the set of transformed values is a vector, and the detector of anomalies is a one-class Support Vector Machine.

This allows a particularly effective detection of the abnormal states of the time windows. Indeed, a one-class Support Vector Machine makes it possible to class in a particularly effective manner vectors from among a set of normal or abnormal vectors. Moreover, a one-class support Vector Machine can be parameterized by the proportion of vectors expected to be abnormal. Thus, the anomaly detector can be parameterized easily, with the aid of this proportion, to detect more or fewer abnormal time windows and to help the operational staff to prioritize the complementary analyses and the interventions according to their available resources.

Advantageously, the set of transformed values is obtained by at least two transformations of the measurements over the time window, and the detector of anomalies is configured to determine a normal or abnormal state of the time window on the basis of the set of transformed values.

This allows the detector of anomalies to detect at what point a set of transformed values is different from the sets gathered previously, on the basis of the set of values, and therefore to detect possible links between transformed values arising from different physical quantities and/or sensors. This solution is particularly efficacious in a water distribution network. Indeed, this makes it possible to detect abnormal simultaneous variations of several physical quantities and/or at several points of a water distribution network.

Advantageously, the set of transformed values is obtained by at least two transformations of the measurements over the time window, and the detector of anomalies is configured to: detect normal or abnormal states of at least two subsets of values transformed respectively by said at least two transformations of the measurements over the time window; detect the normal or abnormal state of the time window on the basis of a combination of said normal or abnormal states of the subsets.

This makes it possible to detect initially the normal or abnormal state of the values arising from each of the transformations, for example of each physical quantity and/or sensor. The normal or abnormal state of the set of transformed values is defined as a function of the normal or abnormal states of each subset. This makes it possible to take into account in a more precise manner the measurements of each physical quantity and/or each sensor. This solution is particularly effective in a natural setting. Indeed, a sensor in a natural setting is more liable to produce false positives: the variability of the values of the physical quantities is more substantial there, and the sensors are liable to undergo slow drifts due for example to fouling, since natural waters are more laden with matter in suspension. Sensors in natural settings are therefore more liable to be faulty and/or to produce noisy measurements. Performing anomaly detection on the measurements arising from each transformation (and therefore from each sensor), and then detecting abnormal windows only if at least two subsets exhibit abnormal values makes it possible to detect anomalies only when the measurements arising from at least two sensors exhibit anomalies.

Advantageously, the processor is configured to calculate an intensity of variation of the physical quantities, and the set of predefined characterization rules comprises a predefined detection rule for detecting a variation of a physical quantity, if the intensity of variation of said physical quantity over the measurements is greater than a threshold of normal variation.

This makes it possible to effectively detect a variation of a physical quantity.

Advantageously, the processor is configured to assign a criticality indicator to the anomaly, as a function of the intensities of the variations of the physical quantities of the subset.

This makes it possible to automatically determine the seriousness of the anomaly, and therefore to undertake the most appropriate corrective actions.

Advantageously, the detection of the variation of the physical quantity detects a variation only if the variation of the physical quantity complies with a direction of variation.

This makes it possible, in the cases where an anomaly is linked with a given direction of variation (increase or decrease), to retain a variation of the physical quantity only if the physical quantity varies in the defined direction.

Advantageously, the processor is configured, if an anomaly is detected, to assign one at least of the following types to the anomaly: a "bacterial growth" type, in case of variation of physical quantities of a subset comprising: a decrease in the chlorine concentration, an increase in temperature, an increase in the total organic carbon content, an increase in the absorbance of Ultraviolet light of wavelength 254 nm, an increase in the number of bacteria; a "water mixture" type, in case of variations of physical quantities of a subset comprising a conductivity, a pH; a temperature; a "colored waters" type, in case of variations the physical quantities of a subset comprising a chlorine concentration, a pH, an increase in color, an increase in turbidity, an increase in the absorbance of Ultraviolet light of wavelength 254 nm; an overspeed, in case of abnormal increase of physical quantities from among a subset comprising turbidity and particles.

These examples allow reliable detection of the above-mentioned types of anomalies.

Advantageously, the processor is configured, if the output of predefined detection rules for detecting a variation of one at least of the physical quantities does not allow the assignment of a type to an anomaly, to assign an unknown type to this anomaly.

This makes it possible to generate in all cases an anomaly associated with a type.

Advantageously, the device comprises an interface for displaying the anomaly and its type to an operator.

This allows an operator to view the anomalies, and make provision if relevant for corrective operations.

Advantageously, the interface is configured to receive from the operator a label relating to the anomaly; the time window of values, and the label relating to the anomaly are added to the training data.

This makes it possible to correct a possible incorrect detection of anomalies, and to improve the training of automatic learning machines for the detection of anomalies.

The invention also describes a method for detecting and characterizing anomalies in a water continuum, comprising: the reception of measurements of a plurality of physical quantities arising from a plurality of sensors of the plurality of physical quantities in the water continuum; the generation of a plurality of time windows of measurements; for each window of said plurality: the obtaining of a set of values transformed by at least one transformation of the measurements over the time window; the detection of a normal or abnormal state of the time window, said detection being parameterized on the basis of sets of transformed values arising from the application of the at least one transformation to time windows of previous measurements of the at least one sensor; the detection of an anomaly in the water continuum, as a function of a number of time windows exhibiting an abnormal state; the execution of a set of predefined detection rules for detecting a variation of one at least of the physical quantities; if an anomaly in the water continuum is detected, the assignment to the anomaly of an anomaly type associated with a variation of a subset of the physical quantities, if the variation of one at least of the quantities of the subset is detected.

The invention also describes a computer program product comprising program code instructions recorded on a medium readable by a computer comprising a processor for the detection of anomalies in a water continuum, said computer program comprising programming means readable by computer for: receiving measurements of a plurality of physical quantities arising from a plurality of sensors of the plurality of physical quantities in the water continuum; generating a plurality of time windows of measurements; for each window of said plurality: obtaining a set of values transformed by at least one transformation of the measurements over the time window; applying a detector of anomalies to the set of transformed values so as to detect a normal or abnormal state of the time window, said detector of anomalies being parameterized on the basis of sets of transformed values arising from the application of the at least one transformation to time windows of previous measurements of the at least one sensor; detecting an anomaly in the water continuum, as a function of a number of time windows exhibiting an abnormal state; executing a set of predefined detection rules for detecting a variation of one at least of the physical quantities; if an anomaly in the water continuum is detected, assigning to the anomaly an anomaly type associated with a variation of a subset of the physical quantities, if the variation of one at least of the quantities of the subset is detected.

BRIEF DESCRIPTION OF THE DRAWINGS

Other characteristics will become apparent on reading the nonlimiting detailed description which follows, given by way of example and with regard to appended drawings in which.

DETAILED DESCRIPTION

In the subsequent description the process according to the invention is mainly illustrated by examples relating to the detection of anomalies in a potable water distribution network. However, the invention is not confined to these examples, and can be applied to any detection of an event linked with the quality of the water, on the basis of measurements of at least two sensors.

Figure 1:
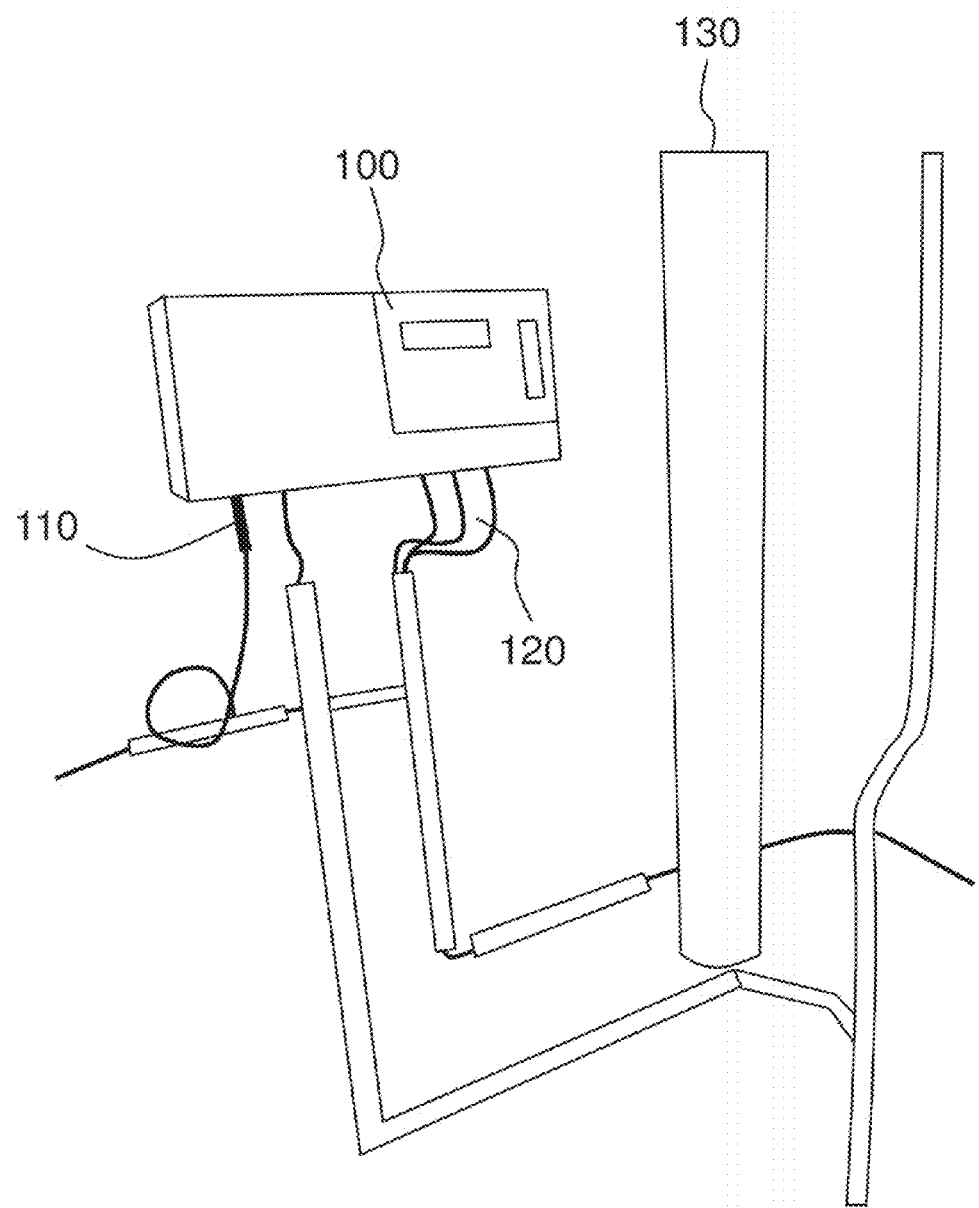
FIG. 1 represents an exemplary probe intended to detect anomalies in water distribution network, according to a set of modes of implementation of the invention.

FIG. 1 represents an exemplary probe intended to detect anomalies in water distribution network, according to a set of embodiments of the invention.

The probe 100 intended to detect anomalies in a water distribution network. The probe can be placed at any site of a water distribution network, for example at the outlet of a potable water production facility, at a reservoir outlet, at a point of consumption, or at any other point.

The probe 100 is connected to pipelines 130 of the water distribution network, for example by a set of sensor cables 120, or connected directly to the network (insertion), and is supplied with electricity 110 or by battery.

The probe 100 can comprise one or more sensors of physical quantities of the water distribution network. For example, the probe 100 can comprise one or more sensors chosen from among sensors of chlorine concentration, temperature, TOC (standing for Total Organic Carbon), UV 254 (absorbance of the water for an ultraviolet light of wavelength 254 nm), conductivity, pH, color, turbidity, number of particles, number of bacteria, dissolved oxygen, chlorophyll a or any sensor of a physical quantity that can characterize the water.

The probe 100 thus makes it possible, in a set of embodiments of the invention, to perform measurements of a set of parameters representative of the quality of the water at a point of the water distribution network.

In a set of embodiments of the invention, the probe 100 comprises communications means so as to transmit the measurements of the embedded sensors. For example, the probe can comprise a wired or radio connection to a server so as to dispatch the measurements to a server configured to detect anomalies in the water distribution network. The probe 100 can thus be coupled to an intelligent water consumption sensor dispatching consumption data by remote reading, by dispatching, in a combined manner, water consumption data and measurements of the sensors.

In a set of embodiments of the invention, the probe comprises a processor configured to detect and characterize, on the basis of the measurements of the sensors, anomalies in the water distribution network.

Examples of detection and characterization of anomalies by a processor will be given hereinbelow, the techniques for detecting and characterizing anomalies described as references to the following figures being applicable to a processor embedded in the probe 100.

Although the probe 100 represents an exemplary probe in a water distribution network, such probes can also be deployed in water in a natural setting, for example in a lake, pond, river or in any other aquatic system, and optionally at various depths.

Figure 2:
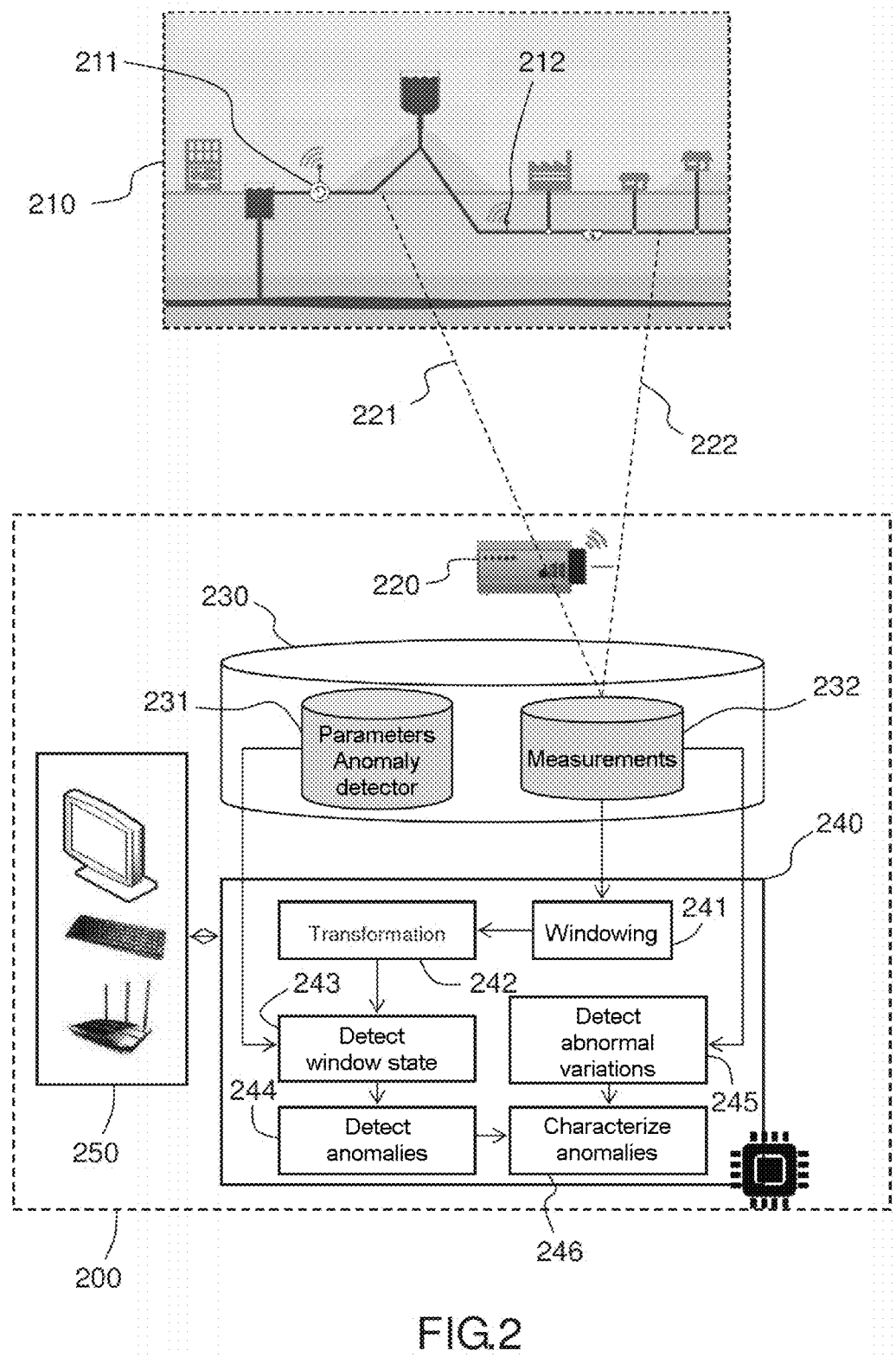
FIG. 2 represents an exemplary device for detecting anomalies in a water continuum according to a set of modes of implementation of the invention.

FIG. 2 represents an exemplary device for detecting anomalies in a water continuum.

The network 210 is a water distribution network equipped with at least one sensor 211, 212 of at least one physical quantity. For example, the sensors 211, 212 can comprise one or more sensors chosen from among sensors of chlorine concentration, temperature, TOC, UV 254, conductivity, pH, color, turbidity, number of particles, number of bacteria, dissolved oxygen, chlorophyll a or any sensor of a physical quantity that can characterize the water. The sensors 211, 212 can be either isolated sensors, or sensors located within multi-sensor probes, such as for example the probe 100 represented in FIG. 1.

Although FIG. 2 represents sensors in a water distribution network, the invention is also applicable to water sensors in a natural setting, for example in a lake, a pond, a river, or more generally in an aquatic system. The sensors can be situated in the same place, or dispersed at several places of the water distribution network or of the natural setting. However, the sensors must be situated in the same water continuum, that is to say that, if the sensors are not situated in the same place, they must be situated in one and the same aquatic system or aquatic systems communicating with one another, in such a way that, when several sensors are present, their measurements can be cross-checked to detect and characterize the anomalies in one and the same water continuum. This condition is fulfilled if the sensors are situated in one and the same water distribution network, at two points of a lake or river, in a lake and an affluent or effluent river flowing into or out of this lake, or more generally at two points of one and the same water continuum. The term "water continuum" can therefore equally well designate a water distribution network or an aquatic system in a natural setting.

The device 200 makes it possible to detect and characterize anomalies in a water continuum, for example the water distribution network 210. It comprises to this effect a processor 240 and at least one link 221 and 222 with the sensors 211, 212. In a set of embodiments of the invention, communication with the sensors 211, 212 can be performed by a system for acquiring measurements, for example a SCADA (Supervisory Control And Data Acquisition) platform. In a set of embodiments of the invention, the communication links 221, 222 are a radio connection with a receiver 220. Numerous other implementations of the communication links are possible. For example, the sensors 220, 221 can dispatch values to a concentrator, which is linked by a radio connection or a cellular telephone connection to a modem in the device 200. Certain parts of the communication link can consist of wired connections. The person skilled in the art can define, without effort, the relevant communication links for a given case of use, for example by selecting one of the communication connections that are well known in the field of water management distribution networks. According to various embodiments of the invention, the device 200 can belong to various types of computerized devices. For example, the device 200 can be a personal computer, a work station, a server, a digital tablet, or any other suitable device.

The system 200 furthermore comprises a storage medium 230. In the example represented in FIG. 2, the storage medium is situated in the device 200. In other embodiments of the invention, the storage media can be situated outside the computerized device. For example, this may entail a shared hard disk, or a remote database, accessible through the requests by the computerized device.

In the example represented in FIG. 2, the storage medium comprises parameters 231 of a detector of anomalies in the water continuum, a database of measurements 232. The parameters 231 make it possible to parametrize a detector of anomalies in the water continuum. As will be described in greater detail hereinafter, the parameters are obtained on the basis of transformations of previous measurements. For example, the parameters 231 can be vectors of previous transformed measurements, or an automatic learning engine configuration obtained with the aid of vectors of previous transformed measurements. The database of measurements 232 is used to store measurements originating from the sensors 211, 212. The measurements comprise notably values of physical quantities measured by the sensor or sensors 211, 212, and a time-stamping with the date/time of the measurements. The storage medium 230 may for example be a hard disk, a solid-state reader, a flash memory or any other known storage type. In other embodiments, the parameters 231 and/or the database of measurements 232 can be stored on various storage media, inside or outside the computerized device 200.

The device 200 can also comprise a set of inputs/outputs 250 such as a screen, a keyboard or a router.

The device 200 comprises a processor 240. Various types of processor are usable within the framework of the invention: the processor may for example be a microprocessor, a microcontroller or a digital signal processor (DSP). The processor is not limited to any processor type or architecture, and can be configured to execute operations by loading executable code elements. The processor can equally well be situated in a probe comprising the at least one sensor or in a personal computer or remote server.

The processor is configured to receive measurements from the at least one sensor 211, 212. In the example of FIG. 2, the processor is configured to read the measurements from the database of measurements 232. However, the processor 240 can also receive the measurements in some other way for example by receiving the measurements directly from the sensors and by storing them in a local work memory.

The processor 240 is moreover configured to generate a plurality of time windows of measurements. According to various embodiments of the invention, the time windows can be either successive time windows, or successive windows which overlap.

Numerous durations of windows are possible. For example, the durations of the time windows can be 5 min, 15 min, 1 h, 6 h, 12 h or 24 h.

The measurements can be sampled at regular intervals within a window. For example, the whole set of sensors can be sampled at the same frequency, and therefore produce measurements simultaneously. In other cases, the sampling frequencies can be variable. For example, certain sensors can be sampled every 5 minutes when others are sampled every 15 minutes. It is then possible to make the timesteps uniform with the aid of data interpolation. The measurements are thus synchronized by taking into account regular timesteps at the smallest available duration of acquisition. This makes it possible to have the same timesteps for all the sensors, sampled at the highest acquisition frequency.

The processor is configured, for each time window, to obtain a set of values transformed by at least one transformation 242 of the measurements over the time window.

The at least one transformation 242 makes it possible to obtain transformed values, certain properties of which may be characteristic of anomalies.

For example, a transformation 242 can consist of a deletion of the long trends (typically daily or weekly) so as to preserve only the fast variations of the measurements of a physical quantity, that is to say that the transformation 242 transforms the measurements into values representative of the variability of the measurements within the time window: the higher the transformed values, the more the time window is affected by fast variations, and the more dispersed the measurements. For example, one of the transformations of the measurements over a window can consist of a filtering of the fast variations, for example of the order of a few hours, with respect to the daily trend, equivalent to a high-pass filter, of the measurements of a physical quantity. Such a transformation makes it possible to preserve just the fast variations of the measurements of a physical quantity, and therefore to detect anomalies linked with an abnormally fast variation of this quantity. For example movements of sediments can be detected by virtue of abnormally fast variations of turbidity.

The transformation of the measurements into values representative of the variability of the measurements within the time window can be carried out by subtracting from each measurement over the time window a median of said measurements over the time window or over a longer time window. This allows effective high-pass filtering, while preserving the information given by each measurement. By way of alternative, the high-pass filtering can also be carried out by other means. For example, it can be carried out by subtracting from each measurement over the time window a mean of said measurements over the time window, or by performing a frequency transform.

The transformation can furthermore preserve only measurements corresponding to a predefined direction of variation. For example, in the case of turbidity measurements, it will be possible to preserve only abrupt increases, which can be caused by movements of sediments. In the case of measurements of chlorine concentration, it will be possible to preserve only the measurements representative of a decrease in the chlorine concentration, able to characterize an increase in the number of bacteria or in the proportion of organic matter. Thus, preserving only the measurements corresponding to an increase in the turbidity can make it possible to discern this anomaly in a more assured manner.

This may for example be performed, in the case mentioned previously where the filtering of the fast variations is carried out by subtracting from each measurement over the time window a median of said measurements over the time window, by preserving after subtraction:
- only the positive or zero values, if the sought-after direction of variation is an increase;
- only the negative or zero values, if the sought-after direction of variation is a decrease.

A transformation can also consist of the application of a slope test over a time window. This makes it possible to detect the slow variations over a time window. Certain anomalies can generate slow variations of certain physical quantities. For example in a potable water network, a slow increase in the number of bacteria, possibly coupled with a slow decline in the chlorine concentration, can signify the risk of appearance of a bacterial growth anomaly. It is advantageous to alert the operational staff regarding this type of ongoing phenomenon so that they are tracked and possibly corrected. In a natural aquatic system, an increase in chlorophyll-a over several days which gives rise firstly to an increase and then a progressive decrease in dissolved oxygen may signify the appearance of algae growth phenomena. They risk being detrimental to aquatic life and to the use of the system, and must therefore be anticipated.

The size of the time window can be adapted to suit the estimated duration of the phenomena in play. For example, a slope test can be performed by comparing the medians of the measurements per day, over a time window of 5 successive days. The slope test may for example be a Mann-Kendall trend test, which is particularly reliable. A slope coefficient may for example be estimated by virtue of a Theil-Sen estimator.

The transformations mentioned hereinabove are applied to time windows of measurements of a physical quantity which arise from a single sensor. However, the invention is not limited to these examples. For example, the person skilled in the art could define transformations making it possible to establish a link between measurements of one and the same physical quantity that arise from two different sensors, so as to obtain transformed values representative of the evolution of a physical quantity in the water continuum. For example, two sensors of dissolved oxygen can be situated upstream and downstream of a river, and a joint transformation of the measurements arising from the two sensors makes it possible to obtain transformed values characterizing the evolution of dissolved oxygen in the river.

For example, at least two of the sensors can be sensors of one and the same physical quantity at two distinct points of the water continuum, and one of the transformations of the measurements over a time window can comprise a time difference between the measurements of the two sensors.

In numerous cases, the flow of the water in the continuum defines temporal correlations between the physical quantities at various points of the continuum. For example, if the water continuum is a river, and if two conductivity sensors are situated, one downstream of the other, the measurements arising from the downstream sensor will be correlated with the measurements of the upstream sensor, through a time difference corresponding to the mean time taken by the water to travel the distance between the upstream sensor and the downstream sensor.

An optimal temporal offset between the measurements of two sensors of one and the same physical quantity at two points of the continuum can be estimated on the basis of the historical data, by performing on the previous measurements cross-correlations between the measurements of the two sensors, by performing a correlation significance test, and by selecting the most substantial peak.

When a transformation of the measurements consists in effecting a time difference according to the optimal temporal offset between the measurements of two sensors of one and the same physical quantity at two distinct points of the continuum, the transformed values will be low if the flow is normal, and if no event impacting the tested physical quantity has occurred between the two sensors.

Conversely, high values could be representative:
- either of a modification of the flow of the water in the continuum, implying that the time taken by the water to travel the space between the two sensors becomes different from the previously calculated optimal temporal offset, the measurements of the physical quantity then no longer being correlated according to this offset;
- or of an event affecting the physical quantity, occurring between the two sensors.

Such a transformation therefore makes it possible not only to detect an anomaly on the basis of measurements distributed in the network, but also to provide location information in respect of a possible anomaly.

The transformation or transformations thus defined make it possible to obtain characteristic transformed values, also called "features", making it possible to detect anomalies. According to various embodiments of the invention, various transformations can be applied over one and the same time window to measurements of various physical quantities. It is also possible to apply several transformations to one and the same physical quantity. The person skilled in the art can thus, knowing the characteristics associated with potential anomalies in the water continuum, define the transformations most suited to the types of measurements available, and to the anomalies sought.

The set of transformed values can take numerous forms, from the moment that the structure of the values transformed over the various time windows remains identical, so as to allow identification of the abnormal sets. It is necessary for the transformations to be applied in a similar manner to the data of the current vector and to the past vectors, serving as training data for the detection of anomalies.

For example, the set of transformed values can be obtained in the form of a vector. If a single transformation is applied, the vector can simply comprise the values transformed on the various parameters over the time window. It can also contain the successive measurements transformed over the time window. If several transformations are applied, the transformed values on completion of each transformation can be concatenated so as to form a single vector.

In a set of embodiments of the invention, the processor is configured to normalize the set of transformed values, so as to detect anomalies on homogeneous values. For example, the processor can be configured to calculate the standard deviation of the values transformed over a time window, and divide all the values of the window by this standard deviation. The processor can also be configured to delete the singular extreme values, with the aim of calculating the features as well as the statistical indicators (standard deviation, mean, median) used for the normalization. Several embodiments are possible to this effect. For example, the processor can be configured to calculate the mean and the standard deviation of the values over the window, and to delete the values which are greater by a predefined number of times the standard deviation than the mean, and/or the values which are lower by this same predefined number of times than the mean, for example the values which are greater than the mean plus three times the standard deviation, or lower than the mean minus three times the standard deviation. Another option consists in deleting a given percentage (for example 5%) of the highest and/or the lowest transformed values over the time window.

When the set of transformed values is obtained by concatenating transformed values arising from several transformations, the normalization of the values can be performed separately on the values arising from each transformation. This makes it possible to obtain a set of homogeneous transformed values, even if the transformations applied and the amplitudes of the initial measurements are very different. No parameter intrinsically dominating the others in the learning space then exists.

In a set of embodiments of the invention, the set of transformed values can also comprise conjunctural data that may have an impact on the measured physical quantities. For example, these data can comprise meteorological data such as hygrometry measurements, measurements of air temperature, of sunshine, of aggregate rain or a number of successive days without rain when the measurements are performed. These parameters affect in particular the water quality of natural aquatic systems. The data in respect of aggregate rain are for example used, via a threshold, to remove the timesteps corresponding to a time of rainy weather from the detection of anomalies.

Figure 3:
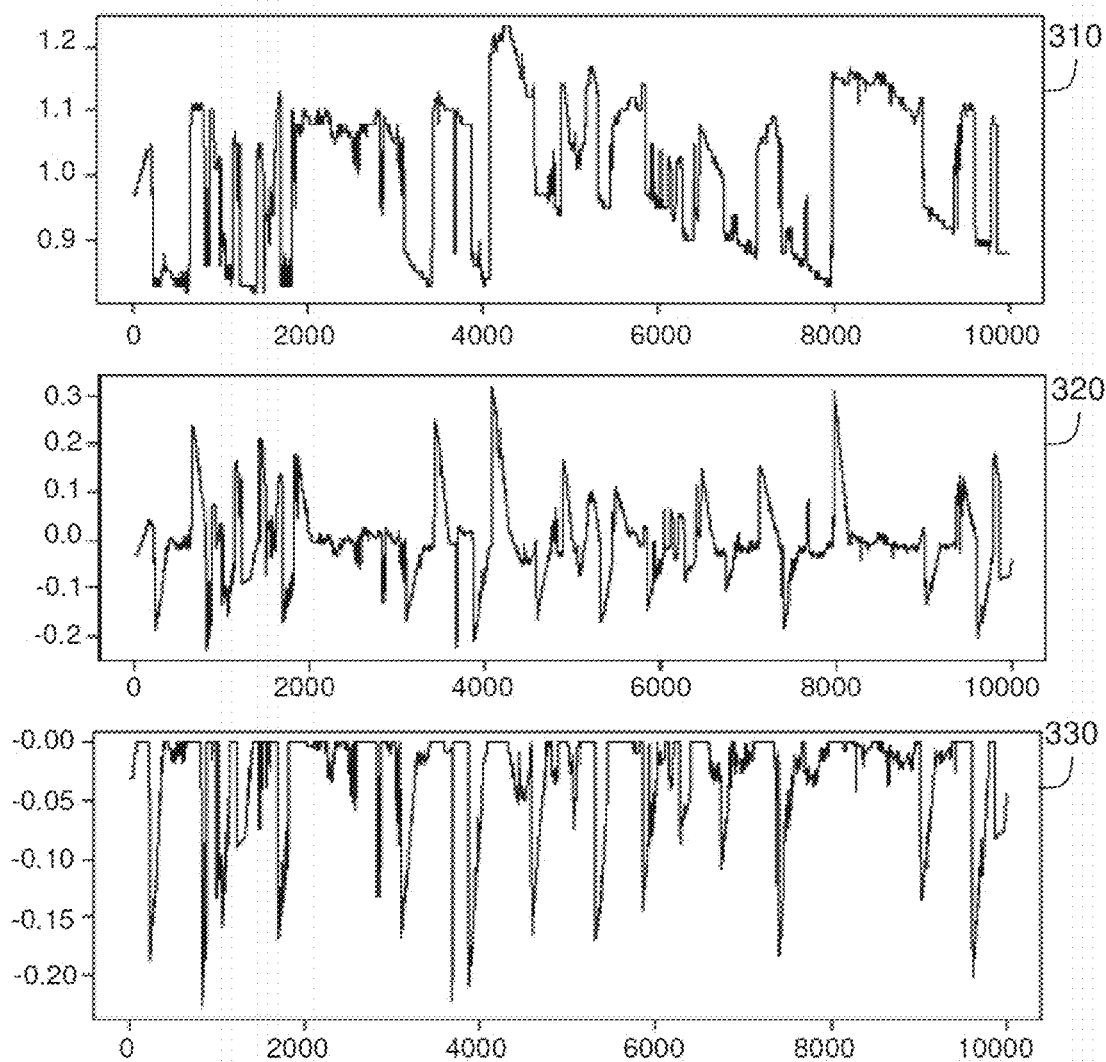
FIG. 3 represents an example of transforming measurements of a physical quantity in a mode of implementation of the invention.

FIG. 3 represents an example of transforming measurements of a physical quantity in an embodiment of the invention.

Curve 310 represents a time window of measurements of chlorine concentration. The horizontal axis represents the elapsed time, in number of 5-minute timesteps. The vertical axis represents the intensities of measurements, in ppm (parts per million).

A first transformation step consists in calculating a median of the measurements over the time window, and in subtracting this median from the measurements, so as to obtain a first level of transformations 320. The transformed values are then representative of the fast variations of the measurements.

A second transformation step consists in preserving only the negative values (therefore representative of a decrease in chlorine concentration). The transformed values 330 therefore make it possible to evaluate a level of fast decrease in chlorine concentration. Since an excessive decrease in chlorine concentration may be caused by a bacterial growth phenomenon, these transformed values can be used to detect this anomaly.

This transformation is given by way of example solely of a transformation according to the invention. The person skilled in the art will readily be able to define the most suitable transformations as a function of the types of anomalies sought, for example by preserving, over a time window, only the fast or slow variations, and only the increases or decreases in a given physical quantity.

Returning to FIG. 2, the processor is moreover configured to apply a detector of anomalies 243 to the set of transformed values so as to detect a normal or abnormal state of the time window, said detector of anomalies being parameterized on the basis of sets of transformed values arising from the application of the at least one transformation to time windows of previous measurements of the at least one sensor.

The detector of anomalies can take various forms. For example, the detector of anomalies can be a set of processor instructions, a software module, or an automatic learning module configured with the aid of previous detections of anomalies. The detector of anomalies is configured to detect, for a time window, whether the set of values is representative of an abnormal state of the time window. To this effect, the detector of anomalies is parameterized with sets of previous transformed values, arising from the at least one transformation 242 at time windows of previous measurements of the at least one sensor 211, 212. Thus, the detector of anomalies is trained with transformed values representative of the water continuum, thereby allowing detection of anomalies that is well suited to the water continuum under study. Although the detector of anomalies improves as the amount of learning data increases, a detector indicating only a normal or abnormal state, on data arising from the same sensors, can be put in place rapidly. In particular, such a detector can detect anomalies as soon as transformed values are significantly different from the transformed values of the learning base. On the other hand, it does not require either to have encountered all the anomalies previously, or that anomalies have been labeled. Thus, the detector of anomalies can be operational very rapidly, as soon as a few transformed measurements are available.

The detection of an abnormal state of the window may for example be performed by the anomaly detector by assigning a score, for example between 0 and 1, to the set of transformed values of a window indicating at what point this set is different from the previous sets of transformed values, and by determining the state of the window to be abnormal if the score is greater than a predefined threshold. It is also possible to detect an abnormal state of a time window, if the transformed values form part of a given percentage of the transformed values that are the most different from the previously gathered values.

Numerous embodiments of the detector of anomalies are possible. In particular, the detector of anomalies can be a machine learning algorithm, which learns in an automatic manner, on the basis of the transformed values obtained previously, the transformed values representative of a normal or abnormal state of a time window.

In a set of embodiments of the invention, the set of transformed values is a vector, and the detector of anomalies is a one-class Support Vector Machine (one-class SVM). This type of detector of anomalies allows particularly effective detection of the abnormal states of the time windows. Indeed, a one-class Support Vector Machine makes it possible to represent in a particularly effective manner the boundary between normal and abnormal (too far from the normal) vectors, so as to determine a level of differences between a vector and the vectors studied previously. Moreover, a one-class Support Vector Machine Machine is parameterized by means of the proportion of vectors expected to be abnormal. A detector of anomalies of one-class Support Vector Machine type exhibits the advantage of providing effective classification of the data into normal or abnormal states. Moreover, it can be put in place very rapidly, with a limited amount of training data.

The one-class Support Vector Machine can thus be parameterized with a variable abnormal vector ratio, for example of between 1/100 and 1/10 000 (that is to say with a proportion of abnormal sets of transformed values of between 1/100 and 1/10 000, the one-class Support Vector Machine then automatically adapting its definition of the abnormal set so as to attain this ratio of abnormal values). The ratio can be adjusted at any time, to detect a larger or smaller number of data sets as being abnormal.

In a set of embodiments of the invention, the set of transformed values is obtained by at least two transformations of the measurements over the time window. Such is the case for example when the set of transformed values is obtained by transforming measurements of several physical quantities and/or measurements arising from several sensors. For example, such a configuration can be obtained if the set of transformed values comprises values arising from a transformation of conductivity measurements, a transformation of pH measurements and a transformation of temperature measurements.

In these cases, the question may arise of the most appropriate way to detect anomalies on this set of transformed values.

In a set of embodiments of the invention, the detector of anomalies is configured to determine a normal or abnormal state of the time window on the basis of the set of transformed values.

This allows the detector of anomalies to detect, on the basis of the set of transformed values arising from different physical quantities and/or sensors, at what point this set is different from the previously gathered sets, and therefore to detect possible links between transformed values arising from different physical quantities and/or sensors. This solution is particularly efficacious in a water distribution network. This solution indeed makes it possible to detect at one and the same time substantial variations on a single parameter or variations which are less substantial but apply to several parameters simultaneously. The detection can thus highlight in a particularly precise manner phenomena affecting several parameters. In the case of potable water networks, the variability of the signal is in general better controlled since it is due to regular business operations. Moreover the sensors are in a cleaner environment, potable water. They generally undergo less drift.

In a set of embodiments of the invention, the set of transformed values is obtained by at least two transformations of the measurements over the time window, and the detector of anomalies is configured to:
  detect normal or abnormal states of at least two subsets of values transformed respectively by said at least two transformations of the measurements over the time window;
  detect the normal or abnormal state of the time window on the basis of a combination of said normal or abnormal states of the subsets.

The various subsets typically correspond to subsets of measurements arising from each sensor and/or each physical quantity over the time window. For example, if a time window comprises conductivity measurements arising from a single sensor, and turbidity measurements arising from two different sensors, the whole set of measurements can be separated into three subsets: a subset of conductivity measurements, and two subsets of turbidity measurements, corresponding to the measurements arising from each of the two sensors.

It is also possible to define subsets according to different rules. For example, a subset could correspond to measurements of one and the same multi-sensor probe, or measurements of one and the same physical quantity arising from several sensors at several different points.

This makes it possible to detect initially the normal or abnormal state of the values arising from each of the transformations, for example each physical quantity and/or sensor. The normal or abnormal state of the set of transformed values is defined as a function of the normal or abnormal states of each subset. This makes it possible to take into account in a differentiated manner the measurements of each physical quantity and/or each sensor. This solution is particularly effective in a natural setting. Indeed the measurements in a natural setting are prone to a more substantial variability of each parameter, as well as to more frequent failures or drifts of the sensors because of the hostility of the medium. It is therefore relevant to seek to ensure that the parameters exhibit abnormal values simultaneously or in a manner which is slightly offset over time, so as to decrease false alerts.

In embodiments of the invention in which the detection of anomalies is performed with the aid of machine learning algorithms, for example a one-class Support Vector Machine, separate learning can be carried out for each of the subsets: the various transformations are applied to each of the time windows of previous measurements used for learning, so as to obtain, for each of these windows, the subsets of corresponding transformed values. Learning is then performed separately, for each subset, on the training data thus obtained. This allows more accurate detection of the abnormal situations on a sensor and/or a physical quantity, by eliminating some of the false alerts that are linked with sensor defects or with the higher natural variability of the measured parameters.

The combining of the normal or abnormal states of the subsets can be done in various ways. For example, an abnormal state of the time window can be detected, if at least one of the subsets has an abnormal state. This makes it possible to detect an anomaly, if the transformed measurements of at least one sensor or a physical quantity are abnormal. It is also possible to detect an abnormal state of the time window, only if all the subsets exhibit an abnormal state, or if at least a given number of subset (for example, at least two subsets out of three) exhibit an abnormal state. In a natural setting, there is no generation of anomaly when there is detection on a single sensor alone, even after temporal smoothing (taking into account of the previous timesteps to fuse the potential anomalies that occurred slightly before).

Figure 4:
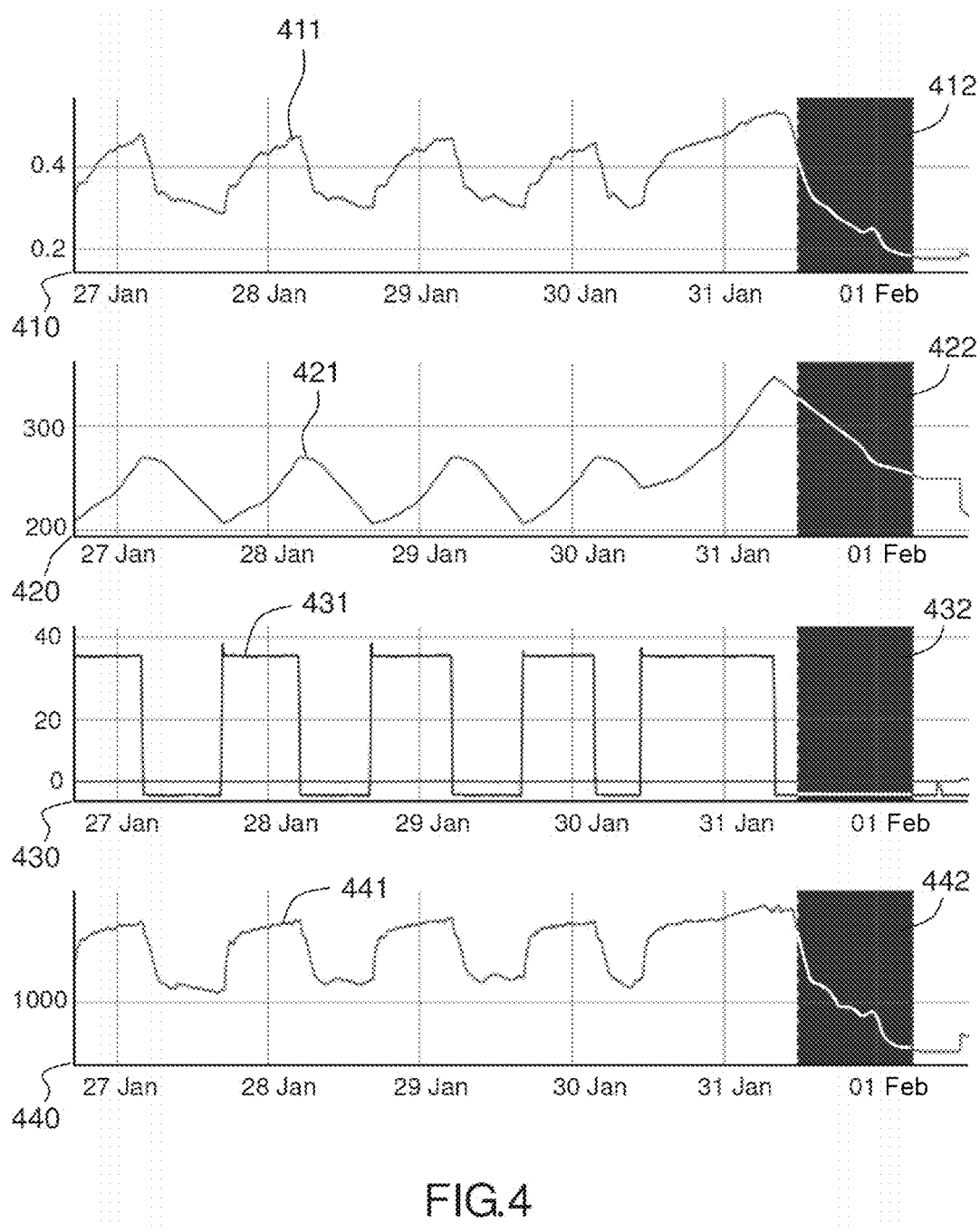
FIG. 4 represents an example of detecting an abnormal time window, in a potable water distribution network.
Figure 4:
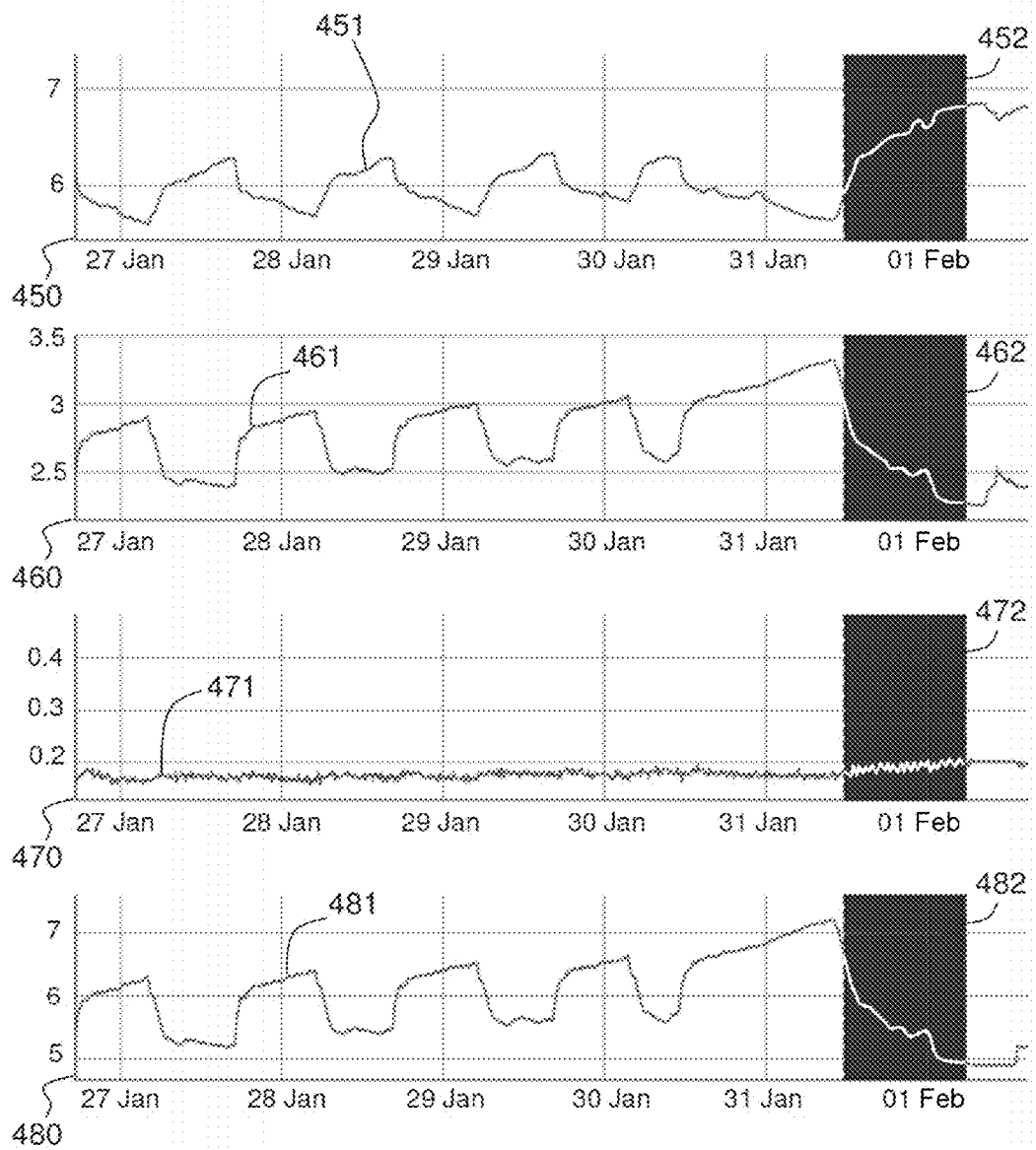

FIG. 4 represents an example of detecting an abnormal time window, in a potable water distribution network.

Curves 410, 420, 430, 440, 450, 460, 470 and 480 represent respectively the evolutions of measurements of 8 sensors of chlorine concentration 411, level of a water reservoir 421, flowrate 431, conductivity 441, temperature 451, TOC 461, turbidity 471 and UV254 481.

These measurements can be obtained on the basis of various sensors, for example the sensors 211, 212.

Here the measurements are performed over a week, between the 26 January 26 and February 1. The measurements are transformed by sliding windows of 24 h, so as to detect abnormal windows. In this example, the measurements follow a regular distribution up to February 1. This regular distribution represents, day after day, the mixing of two sources of water for the filling of a reservoir. Thereafter a problem with the filling of the reservoir causes an anomaly in quality which is visible on numerous parameters over the same time window: the chlorine concentration decreases abruptly 412, the water level in the reservoir rises and then also decreases 422, the water flowrate remains zero for 24 h 432, the conductivity of the water plummets 442, the temperature increases substantially 452, the TOC (Total Organic Carbon concentration) decreases 462, the turbidity increases 472, the absorbance of UV254 decreases 482.

The various transformations of these measurements over the time window make it possible to highlight that the measurements over this window do not follow their usual scheme, and thus to detect an abnormal time window, composed of several abnormal timesteps.

These curves are given solely by way of example, and the person skilled in the art will be able, according to the types of anomalies sought and/or the sensors available, to detect abnormal time windows on another set of physical quantities.

Figure 5:
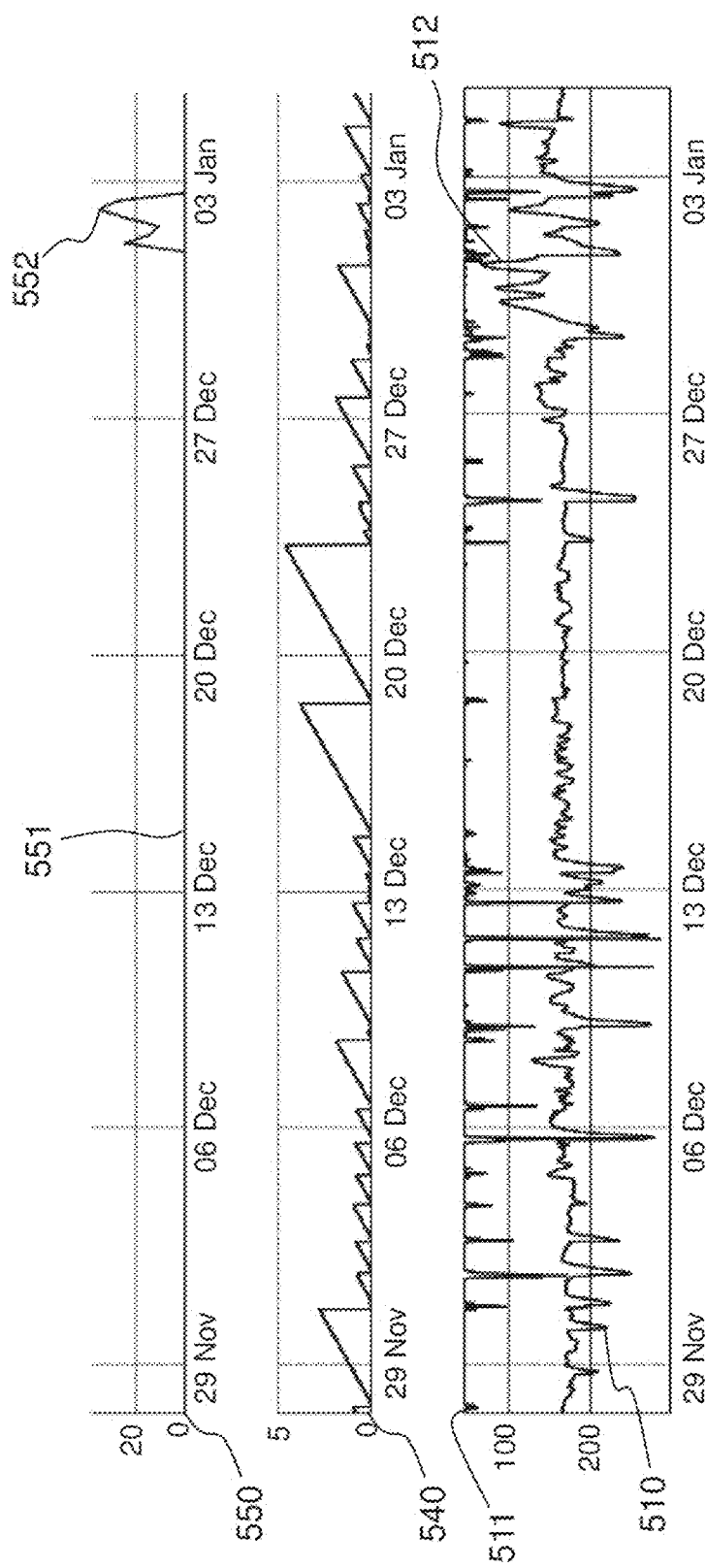
FIG. 5 represents an example of detecting an abnormal time window, in water in a natural setting.
Figure 5:
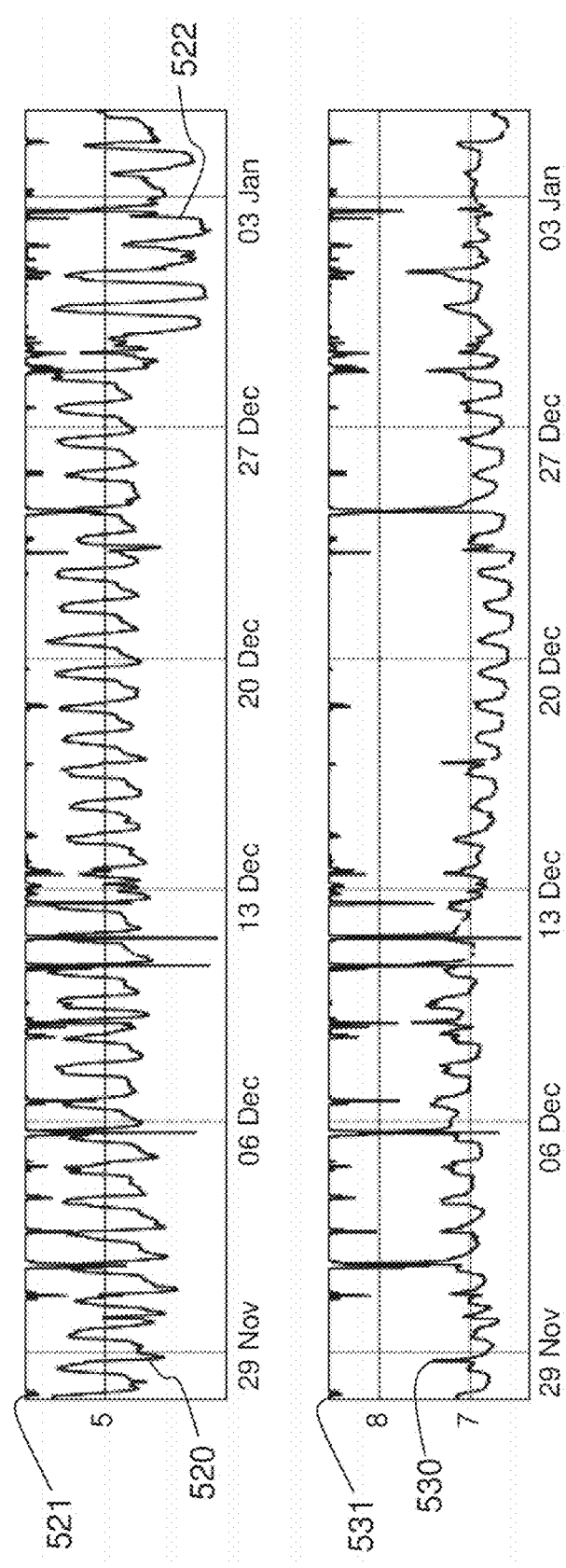

FIG. 5 represents an example of detecting an abnormal time window, in water in a natural setting.

FIG. 5 represents measurements arising from a set of sensors of one and the same probe comprising:
conductivity measurements 510;
measurements of an amount of oxygen dissolution 520;
pH measurements 530.

Conjunctural data (in this instance a number of consecutive days without rain 540, recovered from meteorological data) are also used.

The measurements are transformed so as to obtain transformed values 511, 521, 531 by taking the median of the conductivity, of the amount of dissolved oxygen and of the pH over periods of 6 h.

The detection of anomalies is performed by time windows of 6 h: a time window is analyzed every 6 h. A detector of anomalies is applied to each time window. In this example, a variation is firstly detected on each physical quantity, and an abnormal state of the window is detected, if at least two physical quantities exhibit a variation with fewer than 4 time windows of disparity. This makes it possible to avoid detecting an abnormal window, if a sensor is defective.

Here, the measurements are performed from November 27 to January 5. The measurements are relatively regular in November and December, in particular on removing the timesteps corresponding to rain (inverted blue curves); at the start of January, a variation of the parameters occurs which may reflect pollution by disposal of product into the environment, and which is manifested by an increase 512 in the conductivity, and a decrease 522 in the amount of dissolved oxygen. These anomalies are manifested by abnormally high variations, which make it possible to detect an anomaly of each of these physical quantities over a time window.

Curve 550 represents an evaluation of the intensity of the anomalies over each time window of 6 h. In this example, the intensity of the anomalies is calculated, solely in the case where an anomaly is detected previously, by deducting the aggregate median of the measurements over the history of available data of each physical quantity from the previously calculated transformed values, multiplied by 100 and divided by this same aggregate median so as to normalize these disparities. The maximum over the various physical quantities is then calculated in order to produce the indicator represented on the graph. A value of 0 therefore corresponds to the absence of anomalies. However, this is given solely by way of example only, and other ways of evaluating a criticality of an anomaly which is manifested by substantial disparities between the values within one and the same time window, or with respect to a data history, could be used. It can be observed that the detector of anomalies does not detect any abnormal window in November and December, and then detects a substantial proportion of abnormal windows at the start of January.

These curves are given solely by way of example, and the person skilled in the art will be able, according to the types of anomalies sought and/or the sensors available, to detect abnormal time windows on another set of physical quantities.

Returning to FIG. 2, the processor 240 is moreover configured to detect 244 an anomaly in the water continuum, as a function of a number of time windows exhibiting an abnormal state.

In a set of embodiments of the invention, an anomaly is detected in the water continuum, as soon as a time window exhibits an abnormal state.

In a set of embodiments of the invention, in order to limit the number of false alerts if a single time window is identified as abnormal, an anomaly in the water continuum is detected only if several time windows exhibit an abnormal state. For example, an anomaly can be detected if a predefined number of successive windows (for example 2, 3, 4, 10 . . . ) exhibits an abnormal state. Another option consists in detecting an anomaly, if, over a number of successive time windows, a percentage of successive windows which is greater than a given threshold exhibits an abnormal state. For example, an anomaly can be detected in the water continuum if, among 10 successive time windows, at least 75% exhibit an abnormal state. This makes it possible to generate an alert only if an abnormal state is substantiated. In order to prevent an alert being raised too late, the time windows used can be sliding windows. For example, windows of 6 h of measurements can be generated every hour (thus, a time window comprises 5 h of measurements in common with the previous window). This therefore makes it possible at the same time to detect an anomaly only if the latter is substantiated because it is highlighted on several time windows, to use long time windows, and to avoid too substantial a delay in the detection of anomalies.

The processor 240 is also configured to execute 245 on the measurements a set of predefined detection rules for detecting a variation of one at least of the physical quantities, and if an anomaly is detected, to assign 246 an anomaly type associated with a variation of a subset of the physical quantities to the anomaly, if the variation of one at least of the quantities of the subset is detected.

These rules make it possible to characterize anomalies, if any, in the water continuum. It is possible to use predetermined rules corresponding to known types of anomalies. For example, it is known to the person skilled in the art that a change of water source is manifested by a modification of the conductivity, of the pH and of the temperature of the water. It is therefore possible, in parallel with anomaly detection, to execute predefined rules for anomaly characterization: thus, if an anomaly has been detected, and if in parallel a modification of the conductivity, of the pH and of the temperature of the water has been observed, it can be deduced that this anomaly is a change of water source.

The combination of detection and characterization of anomalies is particularly effective. Indeed:
detection is performed by comparing transformed values of measurements with transformed values arising from previous measurements arising from the same sensors on one and the same water continuum, thereby making it possible to obtain abnormal situation detection which is particularly suited to the water continuum, on the basis of statistical occurrences. Moreover, as indicated hereinabove, such detection can be put in place rapidly with limited training data;
characterization can be based on general rules, since one and the same type of anomaly is manifested, on all water continuums, by a variation of the same physical quantities. Thus, the characterization or the typing of anomalies can be performed on the basis of predefined rules applicable to all aquatic systems, without needing to have been parameterized for a water continuum, or sensors in particular.

Thus, the device according to the invention makes it possible to detect anomalies in a water continuum in a reliable manner suited to the characteristics of the environment under study, and to determine their type, with without needing to have already observed each of the possible anomalies in the water continuum. The device according to the invention can therefore be very rapidly operational, with few prior observations arising from the sensors 211, 212. When a more substantial set of training data is available, and a sufficient number of anomalies have been labeled, the detector of anomalies can be replaced, if detection is thereby improved, by a detector of anomalies detecting the type of anomaly directly.

According to various embodiments of the invention, the rules for detecting variations of the physical quantities can be performed in parallel with the detection of the anomalies, or else solely if an anomaly has been detected.

The detection of variations of physical quantities may for example be performed by calculating an intensity of variation of the physical quantities, and then by comparing this intensity with a threshold, the variation being detected if the intensity of variation is greater than the threshold. This intensity of variation can be calculated in various ways. For example, the variation intensities can be calculated with the aid of the transformed values previously calculated for a physical quantity, for example an intensity of slow variation may have already been calculated on the basis of a slope test and of the calculation of the slope, and it is possible to calculate an intensity of fast variation by applying a moving 95% quantile to values representative of a fast variation, such as disparities of each measurement to a median over a time window. Thus, the mean of the absolute values of the values representative of a fast variation can be calculated. If this mean is greater than a threshold, corresponding here to the limit between the lowest 95%, and the highest 5% of the means of the absolute values of the values representative of a fast variation on a set of previous time windows arising from historical data, a variation of the physical quantity is detected. Here, the mean can be replaced with other characteristic values, such as for example the sum of the absolute values of the values representative of a fast variation. The threshold can be calculated on the basis of the historical data by adding to the median 3 standard deviations. This then represents a high value of the distribution of the data. However, these rules are given solely by way of example, and the person skilled in the art will be able to implement any type of suitable rule making it possible to detect a particularly high variation of a physical quantity, using or otherwise the transformed values calculated by the at least one transformation 242.

According to various embodiments of the invention, the intensity of variations can be calculated for all or some of the physical quantities.

For certain physical quantities, a variation can be considered to be significant or problematic, only for a given direction of variation. For example, a decrease in the chlorine concentration could be considered to be problematic, whilst an increase would not. In a set of embodiments of the invention, a variation of certain physical quantities is retained only if the direction of variation of the physical quantity over the measurements complies with a direction of variation.

In a set of embodiments of the invention, the intensities of variations of the physical quantities also make it possible to determine a criticality of the anomaly. A criticality score can thus be assigned to the anomaly as a function of the intensities of the variations of the physical quantities of the subset associated with the anomaly. This score is calculated according to the previously calculated intensities of the various parameters. These intensities are compared with the intensities calculated over the previous time windows in the data history, solely for the critical parameters. They are then normalized with respect to the robust maximum observed on each parameter, and then the maximum is taken, in order to determine the criticality as a number between 0 and 1.

The person skilled in the art can make provision for numerous assignment rules for assigning a type to an anomaly, as a function of the sensors available, and of the physical quantities associated with the types of anomalies sought.

For example, the following table provides a few examples of types of anomalies that may be assigned, as a function of the abnormal variations of physical quantities:

| Quantities having a variation | Types of anomalies |
| --- | --- |
| Chlorine concentration, temperature, TOC, UV254, number of bacteria | Bacterial Growth |
| Conductivity, pH, temperature | Mixture of water |
| Chlorine concentration, pH, color, turbidity, UV254 | Colored waters |
| Turbidity, particles | Movements of sediments |
| All. | Global anomaly |

These possibilities are given solely by way of example, and the person skilled in the art can choose, for each anomaly, the physical quantities whose variation allows it to be better characterized. The invention thus makes it possible to characterize a substantial number of different anomalies.

According to various embodiments of the invention, a type of anomaly can be detected, if all or some of the associated physical quantities vary. In the example of the table hereinabove, an anomaly could be characterized with the type "water mixture", either if the three quantities conductivity, pH, temperature have an abnormal variation, or if two of the three at least vary.

Once an anomaly has been detected, the latter can, in a set of embodiments of the invention, be displayed to an operator via the interface 250. The interface 250 can notably display the type of anomaly, the place where this anomaly was detected and, if relevant, the criticality of the anomaly.

The detected anomalies can be cross-checked with other sources of information, such as customer complaints, in order to confirm or deny the anomaly.

The operator can thus take all the measures made necessary by the anomaly. In a set of embodiments of the invention, the operator can also validate or otherwise the anomaly, that is to say indicate, after verification, whether or not detection of the anomaly was justified. This makes it possible, when the detector of anomalies is an automatic learning machine, to employ training data which is more reliable, and therefore to improve anomaly detection performance.

In a set of embodiments of the invention, a detected anomaly may generate an event. Various events may be generated, as a function of the measurements arising from various sections of a water distribution network, or various sensors. The events may also be combined with one another, a combination of local events of a water distribution network being able to be interpreted as a global event. If similar events are detected on several sensors, the zone covered can be displayed to the user so that the latter takes the appropriate measures relating thereto. If phenomena are detected at one and the same time at the facility outlet and on the remainder of the network, it is possible to deduce that the anomaly relates to the water treatment facility, and an appropriate event can be generated. It is therefore necessary to investigate at this level and not of that of the network.

Figure 6A:
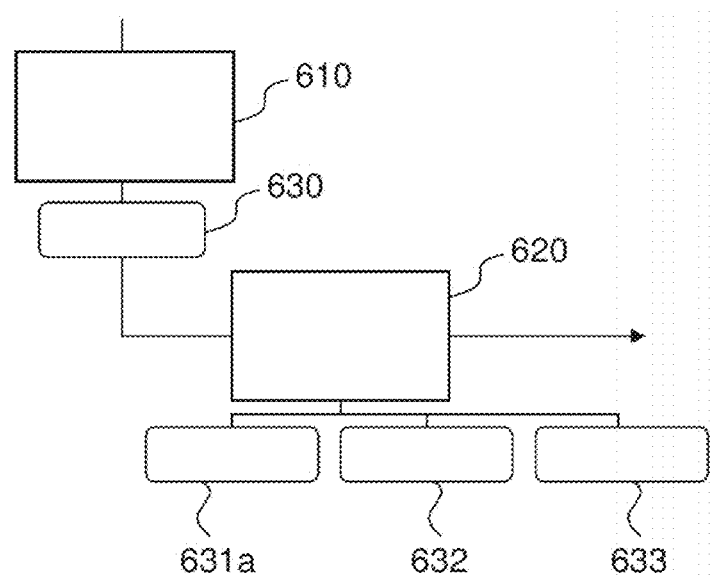
FIGS. 6a and 6b represent two examples of combinations of events on a water distribution network, in a set of modes of implementation of the invention.
Figure 6B:
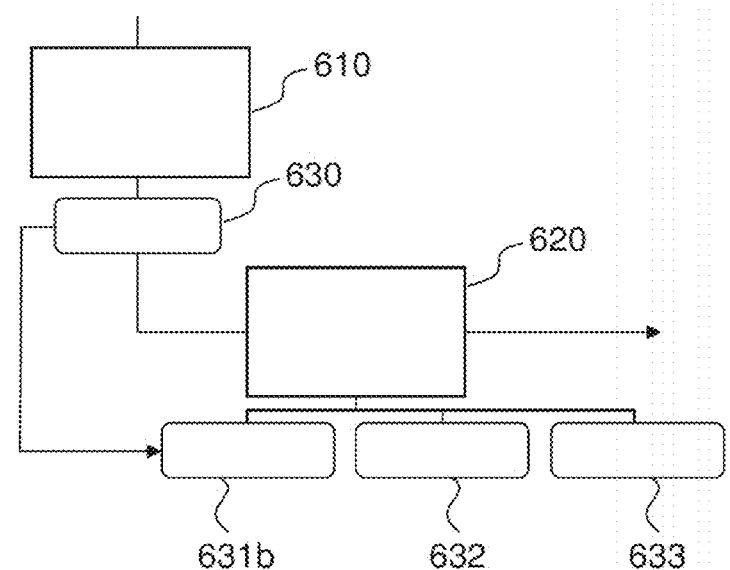

FIGS. 6a and 6b represent two examples of combinations of events on a water distribution network, in a set of modes of implementation of the invention.

In these two examples, a potable water distribution network 620 is situated downstream of a water treatment facility 610. Several generators of events are based on detections of anomalies such as represented in the examples relating to FIG. 2. A first event generator 630 detects possible anomalies on the basis of measurements performed at the outlet of the potable water production facility.

In the example of FIG. 6a, three generators of events 631a, 632, 633 are executed in parallel, on the basis of measurements of physical quantities at three different points of the network. The events thus combined can be combined into events of the network as a whole. For example, a water mixture ought to be visible on several points of one and the same zone.

In the example of FIG. 6b, the event detector 631a has been modified into an event detector 631b, taking into account the occurrence of events 630 at the outlet of the potable water production facility. Thus, when an anomaly is detected by the measurements used by the event detector 631b, the characterization of the type of anomaly or of event depends on the event detection 630. For example, a change in production ought to be able not to be generated on the sensors of the network because it has already been detected at the facility outlet.

These examples demonstrate the ability of the invention to detect anomalies or events in a water distribution network, while taking into account the interactions between the various points of the network, in order to detect anomalies that are more global.

However, the invention is not limited to these examples, and a combination of events such as is described with reference to FIGS. 6a and 6b could for example be applied to the detection of anomalies in a natural setting.

Figure 7:
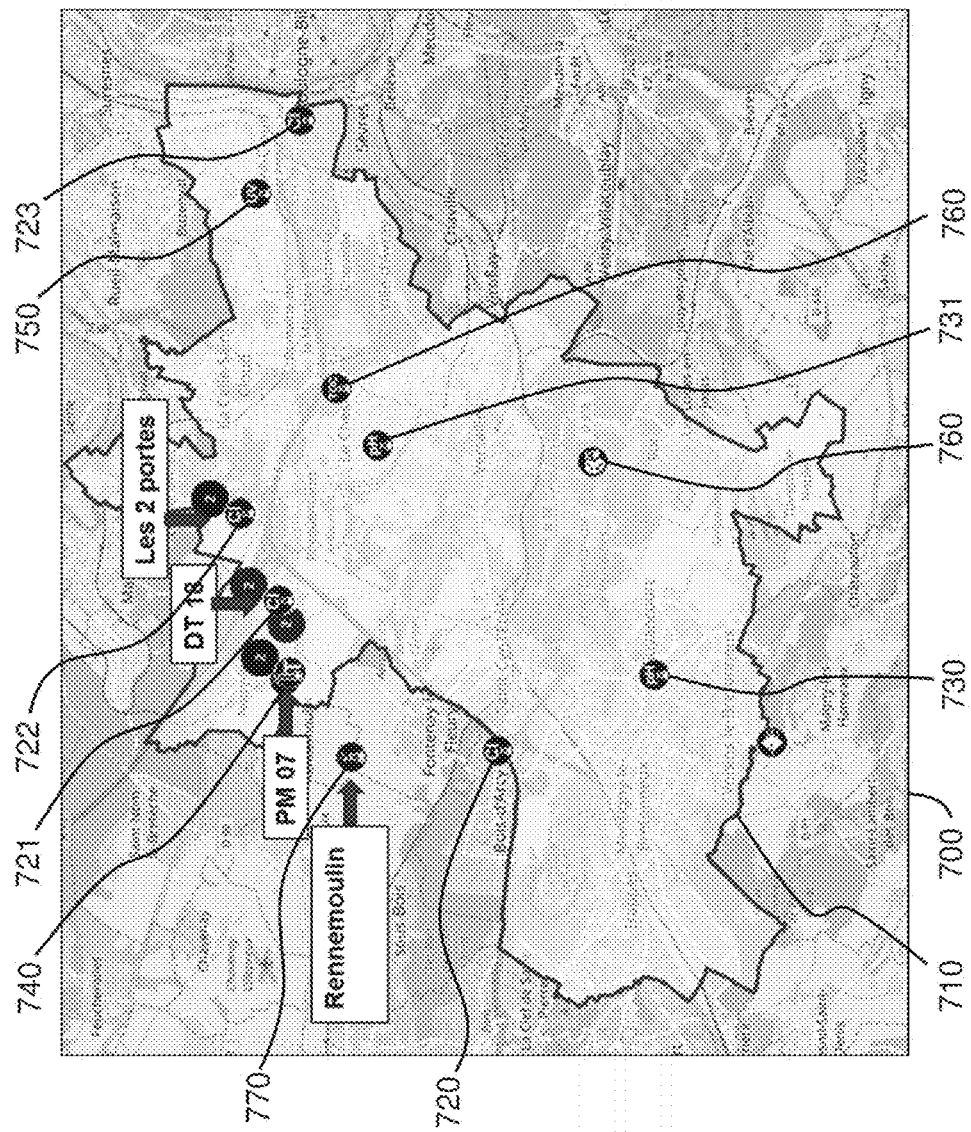
FIG. 7 represents an interface for presenting events occurring in a water distribution network to an operator in a set of modes of implementation of the invention.

FIG. 7 represents an interface for presenting events occurring in a water distribution network to an operator.

The interface 700 is configured to present the anomalies detected by a device according to the invention in a water distribution network to an operator. In this example, the anomalies are detected on a sector 710, and are located on a map. The types of anomalies are represented by various pictograms. In this example, the pictograms represent respectively the positions of the points of measurement: chlorine concentration 720, 721, 722 and 723, of the pH 730 and 731, of the temperature 740, of the absorbance of the water to UV 750, of the TOC 760, of multiparameter probes 760 and of spot tapping-off points 770.

This example demonstrates the ability of the invention to show in a clear manner intuitive to an operator the various anomalies occurring in a water distribution network. However, the invention is not confined to this example, and other types of representation could be used. In the same way, this representation could be used for water in a natural setting.

Figure 8:
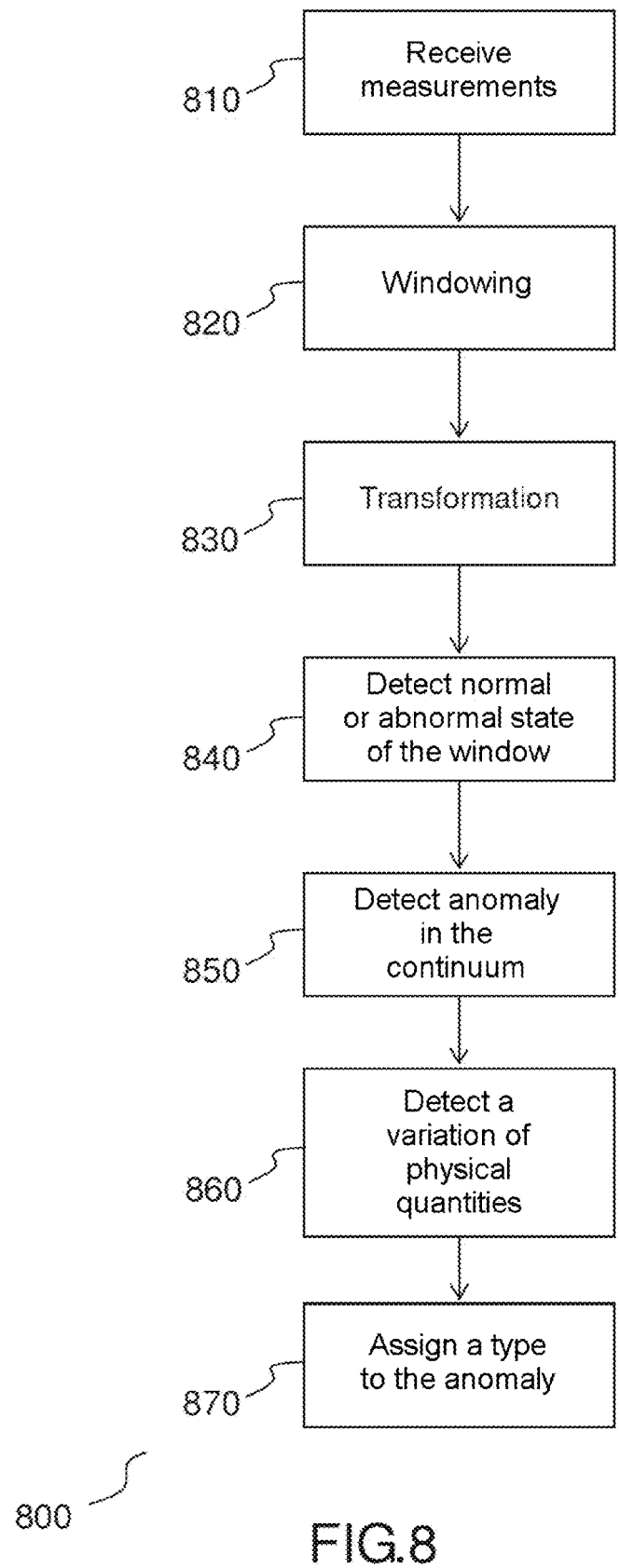
FIG. 8 represents an exemplary method for detecting and characterizing anomalies in a water continuum according to a set of modes of implementation of the invention.

FIG. 8 represents an exemplary method 800 for detecting and characterizing anomalies in a water continuum according to a set of modes of implementation of the invention.

The method 800 comprises the reception 810 of measurements of a plurality of physical quantities arising from a plurality of sensors of the plurality of physical quantities in the water continuum.

The method 800 moreover comprises the generation 820 of a plurality of time windows of measurements.

The method 800 moreover comprises, for each window of said plurality:
the obtaining of a set of values transformed by at least one transformation 830 of the measurements over the time window;
the detection 840 of a normal or abnormal state of the time window, said detection being parameterized on the basis of sets of transformed values arising from the application of the at least one transformation to time windows of previous measurements of the at least one sensor.

In a set of embodiments of the invention, one at least of the transformations 830 is a transformation of the measurements into values representative of the variability of the measurements within the time window.

In a set of embodiments of the invention, the transformation of the measurements into values representative of the variability of the measurements within the time window is carried out by subtracting from each measurement over the time window a median of said measurements over a sliding time window.

In a set of embodiments of the invention, the transformation only preserves measurements corresponding to a predefined direction of variation.

In a set of embodiments of the invention, one at least of the transformations 830 consists of a slope test over the time window.

In a set of embodiments of the invention, the slope test is a Mann-Kendall trend test.

In a set of embodiments of the invention, at least two of the sensors are sensors of one and the same physical quantity at two points of the water continuum, and one of the transformations of the measurements over a time window comprises a time difference between the measurements of the two sensors.

In a set of embodiments of the invention, the set of transformed values is a vector, and the detector of anomalies is a one-class Support Vector Machine.

In a set of embodiments of the invention, the set of transformed values is obtained by at least two transformations of the measurements over the time window, and the detection of anomalies determines a normal or abnormal state of the time window on the basis of the set of transformed values.

In a set of embodiments of the invention, the set of transformed values is obtained by at least two transformations of the measurements over the time window, and the detection of anomalies:
detects normal or abnormal states of at least two subsets of values transformed respectively by said at least two transformations of the measurements over the time window;
detects the normal or abnormal state of the time window on the basis of a combination of said normal or abnormal states of the subsets.

The method 800 moreover comprises the detection 850 of an anomaly in the water continuum, as a function of a number of time windows exhibiting an abnormal state.

The method 800 moreover comprises the execution 860 of a set of predefined detection rules for detecting a variation of one at least of the physical quantities.

In a set of embodiments of the invention, the method 800 comprises a calculation of an intensity of variation of the physical quantities, and the set of predefined characterization rules comprises a predefined detection rule for detecting a variation of a physical quantity, if the intensity of variation of said physical quantity over the measurements is greater than a threshold of normal variation.

In a set of embodiments of the invention, the detection of the variation of the physical quantity detects a variation only if the variation of the physical quantity complies with a direction of variation.

The method 800 finally comprises, if an anomaly is detected, the assignment 870 to the anomaly of an anomaly type associated with a variation of a subset of the physical quantities, if the variation of one at least of the quantities of the subset is detected.

In a set of embodiments of the invention, the method 800 comprises the assignment of a criticality indicator to the anomaly, as a function of the intensities of the variations of the physical quantities of the subset.

In a set of embodiments of the invention, the method 800 comprises, if an anomaly is detected, the assignment to the anomaly of one at least of the following types:
- a "bacterial growth" type, in case of variation of physical quantities of a subset comprising: a decrease in the chlorine concentration, an increase in temperature, an increase in the total organic carbon content, an increase in the absorbance of Ultraviolet light of wavelength 254 nm, an increase in the number of bacteria;
- a "water mixture" type, in case of variations of physical quantities of a subset comprising a conductivity, a pH; a temperature;
- a "colored waters" type, in case of variations of physical quantities of a subset comprising a chlorine concentration, a pH, an increase in color, an increase in turbidity, an increase in the absorbance of Ultraviolet light of wavelength 254 nm;
- an overspeed, in case of abnormal increase of physical quantities from among a subset comprising turbidity and particles.

In a set of embodiments of the invention, the method 800 comprises, if the output of predefined detection rules for detecting a variation of one at least of the physical quantities does not allow the assignment of a type to an anomaly, the assignment to this anomaly of an unknown type.

In a set of embodiments of the invention, the method 800 comprises a step of using an interface to display the anomaly and its type to an operator.

In a set of embodiments of the invention, method 800 comprises:
- the use of the interface to receive from the operator a label relating to the anomaly;
- the addition of the time window of values, and of the label relating to the anomaly to the training data.

The method 800 thus makes it possible to detect various types of anomalies in a water continuum, and to assign types to them. All the embodiments described with reference to FIGS. 2 to 7 are applicable to the method 800.

The examples hereinabove demonstrate the ability of the invention to detect events or anomalies linked with water quality. They are, however, given only by way of example and in no case limit the scope of the invention, defined in the claims hereinbelow.

The invention claimed is:

1. A device able to detect and characterize anomalies in a water continuum, comprising:
   at least one communication link, respectively to at least one sensor of at least one physical quantity in the water continuum;
   a processor configured to:
   receive measurements from the at least one sensor through the at least one communication link;
   generate a plurality of time windows of the measurements;
   for each time window of said plurality:
   obtain a set of values transformed by at least one transformation of the measurements over the time window;
   apply a detector of anomalies to the set of transformed values so as to detect a normal or abnormal state of the time window, said detector of anomalies being parameterized on the basis of sets of transformed values arising from the application of the at least one transformation to time windows of previous measurements of the at least one sensor;
   detect an anomaly in the water continuum, as a function of a number of time windows exhibiting an abnormal state;
   execute on the measurements a set of predefined detection rules for detecting a variation of at least one of the physical quantities;
   if an anomaly in the water continuum is detected, assign to the anomaly an anomaly type associated with a variation of a predefined subset of the physical quantities, if the variation of one at least of the quantities of the subset is detected;
   wherein the rules for detecting a variation of the at least one of the physical quantities is performed in parallel with the detection of the anomaly such that the predefined detection rules are not applied to detect the anomaly.

2. The device as claimed in claim 1, wherein one of the transformations of the measurements over a time window is a transformation of the measurements into values representative of the variability of the measurements within the time window.

3. The device as claimed in claim 2, wherein the transformation of the measurements into values representative of the variability of the measurements within the time window is carried out by subtracting from each measurement over the time window a median of said measurements over a sliding time window comprising at least said time window.

4. The device as claimed in claim 1, wherein the transformation preserves only measurements corresponding to a predefined direction of variation.

5. The device as claimed in claim 1, wherein one of the transformations of the measurements over a time window consists of a slope test over the time window.

6. The device as claimed in claim 1, wherein at least two of the sensors are sensors of one and the same physical quantity at two points of the water continuum, and one of the transformations of the measurements over a time window comprises a time difference between the measurements of the two sensors.

7. The device as claimed in claim 1, wherein the set of transformed values is a vector, and the detector of anomalies is a one-class Support Vector Machine.

8. The device as claimed in claim 1, wherein the set of transformed values is obtained by at least two transformations of the measurements over the time window, and the detector of anomalies is configured to determine a normal or abnormal state of the time window on the basis of the set of transformed values.

9. The device as claimed in claim 1, wherein the set of transformed values is obtained by at least two transformations of the measurements over the time window, and the detector of anomalies is configured to:

detect normal or abnormal states of at least two subsets of values transformed respectively by said at least two transformations of the measurements over the time window;

detect the normal or abnormal state of the time window on the basis of a combination of said normal or abnormal states of the subsets.

10. The device as claimed in claim 1, wherein the processor is configured to calculate an intensity of variation of the physical quantities, and the set of predefined characterization rules comprises a predefined detection rule for detecting a variation of a physical quantity, if the intensity of variation of said physical quantity over the measurements is greater than a threshold of normal variation.

11. The device as claimed in claim 10, wherein the processor is configured to assign a criticality indicator to the anomaly, as a function of the intensities of the variations of the physical quantities of the subset.

12. The device as claimed in claim 1, wherein the detection of the variation of the physical quantity detects a variation only if the variation of the physical quantity complies with a direction of variation.

13. The device as claimed in claim 1, wherein the processor is configured, if an anomaly is detected, to assign one at least of the following types to the anomaly:
   a "bacterial growth" type, in case of variation of physical quantities of a subset comprising: a decrease in the chlorine concentration, an increase in temperature, an increase in the total organic carbon content, an increase in the absorbance of Ultraviolet light of wavelength 254 nm, an increase in the number of bacteria;
   a "water mixture" type, in case of variations of physical quantities of a subset comprising a conductivity, a pH; a temperature;
   a "colored waters" type, in case of variations the physical quantities of a subset comprising a chlorine concentration, a pH, an increase in color, an increase in turbidity, an increase in the absorbance of Ultraviolet light of wavelength 254 nm;
   an overspeed, in case of abnormal increase of physical quantities from among a subset comprising turbidity and particles.

14. The device as claimed in claim 1, wherein the processor is configured, if the output of predefined detection rules for detecting a variation of one at least of the physical quantities does not allow the assignment of a type to an anomaly, to assign an unknown type to this anomaly.

15. The device as claimed in claim 1, comprising an interface for displaying the anomaly and its type to an operator.

16. The device as claimed in claim 15, wherein:
   the interface is configured to receive from the operator a label relating to the anomaly;
   the time window of values, and the label relating to the anomaly are added to the training data.

17. A method for detecting and characterizing anomalies in a water continuum, comprising:
   the reception of measurements of a plurality of physical quantities arising from a plurality of sensors of the plurality of physical quantities in the water continuum;
   the generation of a plurality of time windows of measurements;
   for each window of said plurality:
      the obtaining of a set of values transformed by at least one transformation of the measurements over the time window;
      the detection of a normal or abnormal state of the time window, said detection being parameterized on the basis of sets of transformed values arising from the application of the at least one transformation to time windows of previous measurements of the at least one sensor;
   the detection of an anomaly in the water continuum, as a function of a number of time windows exhibiting an abnormal state;
   the execution of a set of predefined detection rules for detecting a variation of at least one of the physical quantities;
   if an anomaly in the water continuum is detected, the assignment to the anomaly of an anomaly type associated with a variation of a predefined subset of the physical quantities, if the variation of one at least of the quantities of the subset is detected;
   wherein the rules for detecting the variation of the at least one of the physical quantities is performed in parallel with the detection of the anomaly in the water continuum such that the predefined detection rules are not applied to detect the anomaly.

18. A computer program product comprising program code instructions recorded on a non-transitory medium readable by a computer comprising a processor for the detection of anomalies in a water continuum, said computer program comprising programming means readable by computer for:
   receiving measurements of a plurality of physical quantities arising from a plurality of sensors of the plurality of physical quantities in the water continuum;
   generating a plurality of time windows of measurements;
   for each window of said plurality:
      obtaining a set of values transformed by at least one transformation of the measurements over the time window;
      applying a detector of anomalies to the set of transformed values so as to detect a normal or abnormal state of the time window, said detector of anomalies being parameterized on the basis of sets of transformed values arising from the application of the at least one transformation to time windows of previous measurements of the at least one sensor;
   detecting an anomaly in the water continuum, as a function of a number of time windows exhibiting an abnormal state;
   executing a set of predefined detection rules for detecting a variation of at least one of the physical quantities;
   if an anomaly in the water continuum is detected, assigning to the anomaly an anomaly type associated with a variation of a predefined subset of the physical quantities, if the variation of one at least of the quantities of the subset is detected;
   wherein the rules for detecting the variation of the at least one of the physical quantities is performed in parallel with the detection of the anomaly in the water continuum such that the predefined detection rules are not applied to detect the anomaly.

* * * * *